United States Patent
Bryzgalov et al.

(10) Patent No.: US 11,686,674 B2
(45) Date of Patent: Jun. 27, 2023

(54) GAS DETECTOR

(71) Applicant: ASAHI KASEI MICRODEVICES CORPORATION, Tokyo (JP)

(72) Inventors: Maksym Bryzgalov, Delsbo (SE); Mats Olsson, Delsbo (SE); Henrik Rodjegard, Delsbo (SE); Hans Martin, Delsbo (SE)

(73) Assignee: Asahi Kasei Microdevices Corporation, Tokyo (JP)

( * ) Notice: Subject to any disclaimer, the term of this patent is extended or adjusted under 35 U.S.C. 154(b) by 30 days.

(21) Appl. No.: 17/385,982

(22) Filed: Jul. 27, 2021

(65) Prior Publication Data
US 2022/0034797 A1 Feb. 3, 2022

(30) Foreign Application Priority Data

Jul. 30, 2020 (JP) .................................. 2020-129672
Jun. 30, 2021 (JP) .................................. 2021-108741

(51) Int. Cl.
*G01N 21/3504* (2014.01)
*G01N 33/00* (2006.01)

(52) U.S. Cl.
CPC ..... *G01N 21/3504* (2013.01); *G01N 33/0027* (2013.01); *G01N 2201/0231* (2013.01)

(58) Field of Classification Search
CPC ........... G01N 21/3504; G01N 33/0027; G01N 2201/0231
See application file for complete search history.

(56) References Cited

U.S. PATENT DOCUMENTS

2020/0116632 A1* 4/2020 Henderson ............. G01N 21/61

FOREIGN PATENT DOCUMENTS

JP     H09-79980 A     3/1997

* cited by examiner

*Primary Examiner* — Kiho Kim
(74) *Attorney, Agent, or Firm* — Morgan, Lewis & Bockius LLP (57) ABSTRACT

The present invention is directed to a gas detector configured to improve response speed of a gas sensor. A gas detector includes a housing, a gas sensor main body installed in the housing, and a partition wall provided in the housing and limiting the surrounding of the gas sensor main body to separate from the other area. The housing or the partition wall includes an opening portion directly connected from the outside to an area inside the partition wall.

8 Claims, 8 Drawing Sheets

GAS DETECTOR

TECHNICAL FIELD

The present invention relates to a gas detector for measuring the concentration of a gas to be measured in the atmosphere, and in particular to a technology for improving the response speed of a gas sensor provided in a housing of this type of gas detector.

BACKGROUND ART

As devices for measuring the concentration of a gas to be measured in the atmosphere, there are conventionally known gas detectors provided with a gas sensor of non-dispersive infrared type that measures gas concentration by utilizing the fact that the wavelength of infrared light absorbed varies depending on the type of gas and detecting the amount of the infrared absorption.

Known examples of this type of device are gas detectors (e.g., see PTL 1).

CITATION LIST

Patent Literature

PTL 1: JP H09-079980 A

SUMMARY OF INVENTION

Technical Problem

Here, to meet safety standards imposed on such gas detectors, a faster response gas sensor is desired. On the other hand, in order to improve the response speed of a gas sensor provided in a gas detector, the air around a gas sensor main body in the detector housing needs to be replaced quickly. For example, one possible way is to install a fan to generate an air flow. However, there is a limit to the improvement of exhaust performance in the housing, and also, a thermally unstable situation may occur.

Accordingly, the present invention has been made in view of such problems, and it is an object of the present invention to provide a gas detector capable of improving the response speed of a gas sensor in a detector housing.

Solution to Problem

To achieve the above object, a gas detector according to one aspect of the present invention includes a housing, a gas sensor main body installed in the housing, and a partition wall provided in the housing and limiting a surrounding of the gas sensor main body to separate from an other area, in which the housing or the partition wall includes an opening portion directly connected from an outside to an area inside the partition wall.

In the gas detector according to the one aspect of the present invention, the opening portion connecting the inside of the partition wall to the outside is provided in the partition wall limiting the surrounding of the gas sensor main body in the housing to separate from the other area in the housing and in the housing. Therefore, compared to the structure that replaces the entire air in the housing, air in the partition wall surrounding the surrounding of the gas sensor main body can be replaced more quickly. This allows for obtaining of a gas sensor response speed that satisfies the safety standards imposed on gas detectors by the simple configuration of the housing structure.

Additionally, to achieve the object, a gas detector according to another one aspect of the present invention includes a housing, a gas sensor main body installed in the housing, and a metal cage arranged to surround a surrounding of the gas sensor main body and heated by a heater.

In the gas detector according to the other one aspect of the present invention, the metal cage arranged to surround the surrounding of the gas sensor main body and heated by a heater is provided in the housing, which allows the gas sensor main body and a space therearound to be heated efficiently. Accordingly, there can be obtained a space thermally stable in as narrow a range as possible around the gas sensor main body, thereby enabling improvement in response speed of the gas sensor in the housing.

Advantageous Effects of Invention

As described above, according to the present invention, the response speed of the gas sensor in the housing can be improved.

DESCRIPTION OF EMBODIMENTS

Hereinafter, embodiments and Examples (including modifications) of the present invention will will be described with appropriate reference to the drawings. It should be noted that the drawings are schematic, and therefore, relationships and ratios between thicknesses and planar dimensions, and the like are different from actual ones, and the dimensional relationships and ratios are partially different from each other among the drawings.

Additionally, the following embodiments and examples exemplify devices and methods for embodying the technological ideas of the present invention, and the technological ideas of the invention is not limited to the materials, shapes, structures, arrangements, and the like of the constituent components to the embodiments below.

First Embodiment

Figure 1:
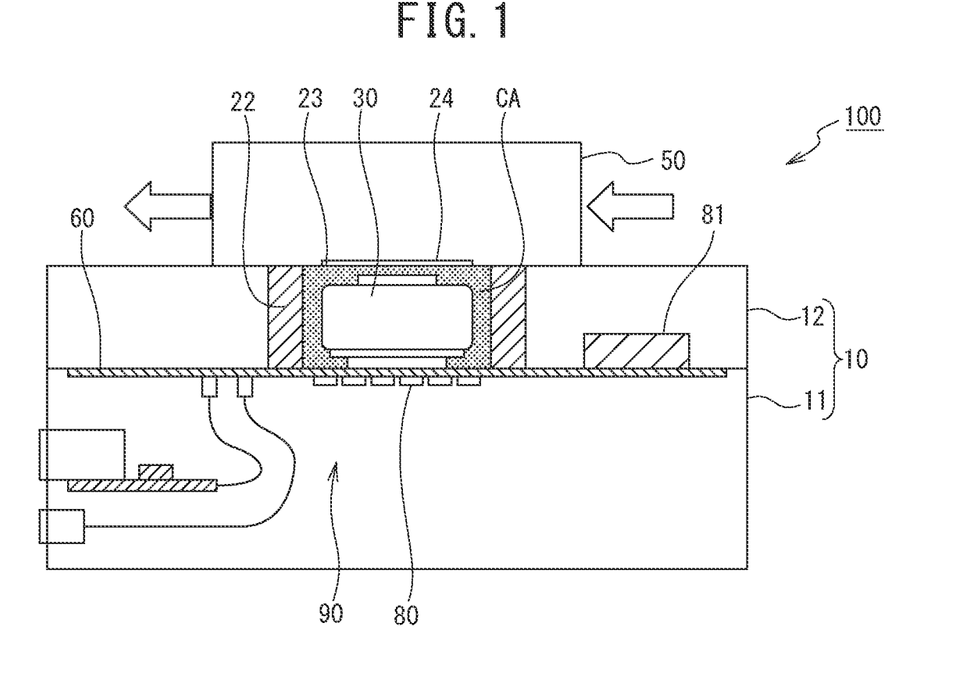
FIG. 1 is a schematic sectional view illustrating a first embodiment of a gas detector according to one aspect of the present invention.

First, a gas detector of a first embodiment will be described. FIG. 1 illustrates a schematic sectional view of the gas detector of the first embodiment.

As illustrated in the drawing, a gas detector 100 of the first embodiment includes a housing 10, a gas sensor main body 30 provided in the housing 10, and a partition wall 22 surrounding to define a cavity space CA having a small capacity around the gas sensor main body 30. In the drawing, the area of the cavity space CA defined is indicated by shading. Note that in the gas detector 100 of the first embodiment, the cavity space CA is a space surrounded by a part of the housing 10 and the partition wall 22.

The gas sensor main body 30 includes a non-dispersive infrared optical cell that measure the concentration of a gas by utilizing the fact that the wavelength of absorbed infrared light varies depending on the type of the gas and detecting the amount of the infrared absorption (the same applies to other aspects).

In addition, although a detailed description will be omitted, the optical cell is provided with an inlet/outlet for a gas to be measured at the top, and includes a cover portion with a cavity formed thereinside and an element portion including a reflector, a light emitter, and a light receiver provided in the cavity of the cover portion so that a predetermined optical path is formed (the same applies below).

The housing 10 of the first embodiment includes a base portion 11 on a lower side and a cover portion 12 on an upper side. A PCB substrate 60 is sandwiched and fixed between the base portion 11 and the cover portion 12. At an upper center of the cover portion 12 is provided the inlet/outlet for a gas to be measured, where there is provided an opening portion 23 that is directly connected from an outside to the cavity space CA, which is an area inside the partition wall 22, and a particle filter 24 for gas exchange is attached to the opening portion 23. In other words, the opening portion 23 does not connect the cavity space CA and the other area, but directly connects the outside of the housing 10 to the cavity space CA.

The particle filter 24 and a portion therearound are covered with an inlet cover 50, which prevents infiltration of dust particles and raindrops into the particle filter 24. Note that while arrows put at the inlet cover 50 indicate an airflow image of a gas to be measured when introduced and discharged.

The gas sensor main body 30 is mounted at the center of the PCB substrate 60, and a PID regulator 81 is mounted at a side of the PCB substrate 60. Additionally, on a back surface of the PCB substrate 60, a heater 80 formed by a resistance heater, a heating transistor, or the like is mounted at a position facing the gas sensor main body 30.

In the example of the first embodiment, the gas detector 100 of the first embodiment allows the partition wall 22 to surround the gas sensor main body 30 housed in the housing 10, as a compartment that limits the surrounding of the gas sensor main body 30 of the above-described non-dispersive infrared type to separate the area from the other area in the housing 10.

Additionally, the other areas that are areas other than the cavity space CA, i.e., an area outside the partition wall 22 in the cover portion 12 on the upper side and an area 90 that is on a back surface side of the PCB substrate 60 and defined by the base portion 11 are used as other areas in which auxiliary electronic devices, electronic components such as interfaces, a communication unit, and a heater controller, and members such as connectors required for the gas detector are arranged.

Here, the area other than the cavity space CA is surrounded all around by the housing 10 and the partition wall 22, and provided with no inlet/outlet for a gas to be measured. Only the cavity space CA is connected to the outside by the opening portion 23. However, the inlet/outlet for the gas to be measured may be provided in the area other than the cavity space CA.

The cavity space CA is sufficiently smaller than the other area, and a volume of the cavity space CA is equal to or less than half a volume of the other area. Note that, more preferably, the volume of the cavity space CA is equal to or less than one-third the volume of the other area. In addition, lengths of the cavity space CA in height, width, and depth directions are equal to or less than twice the respective lengths of the gas sensor main body 30 in height, width, and depth directions.

Next, functions and effects of the gas detector 100 of the first embodiment will be described.

As described above, the gas detector 100 of the first embodiment includes the partition wall 22 for the gas sensor main body 30 provided in the housing 10 and limiting the surrounding of the gas sensor main body 30 to separate from the other area, and the housing 10 is provided with the opening portion 23 directly connected from the outside to the cavity space CA.

As a result, in the gas detector 100 of the first embodiment, the partition wall 22 defines the cavity space CA having a small capacity around the gas sensor main body 30, and a gas to be measured is directly introduced and discharged through the opening portion 23 into and from the cavity space CA, so that the surrounding of the gas sensor main body 30 can be quickly ventilated, separately from the other area. This allows for fast response of the gas sensor main body 30 in the housing 10.

Additionally, since the volume of the cavity space CA is equal to or less than half the volume of the other area, faster response of the gas sensor main body 30 in the housing 10 is possible.

In addition, since the gas detector 100 includes the inlet cover 50 covering the opening portion 23, dust particles and raindrops can be prevented from infiltrating into the opening portion 23 even though the gas detector 100 includes the opening portion 23 directly connected from the outside to the cavity space CA.

Furthermore, the electronic components are arranged in the other area of the housing 10, and only the cavity space CA is connected to the outside by the opening portion 23. Therefore, introduction and discharge of the gas to be measured is quickly performed in the cavity space CA, but not performed in the other area, and dust particles and raindrops can also be prevented from infiltrating into the other area, which can reduce failure rates of the electronic components.

Second Embodiment

Figure 2A:
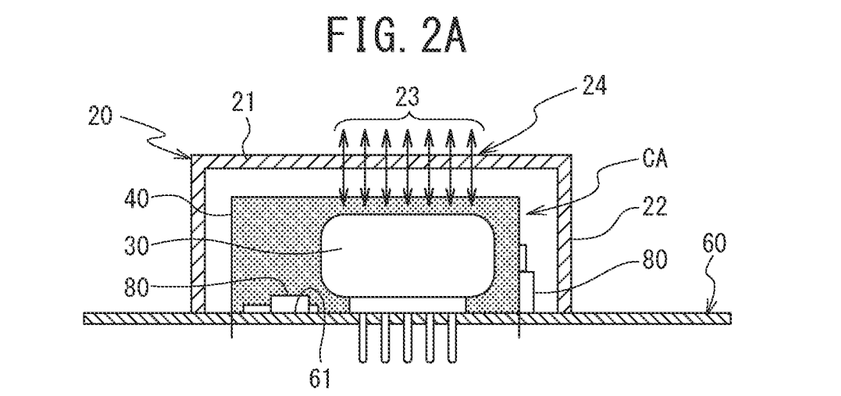
FIGS. 2A and 2B are schematic sectional views illustrating a second embodiment of the gas detector according to the one aspect of the present invention.
Figure 2B:
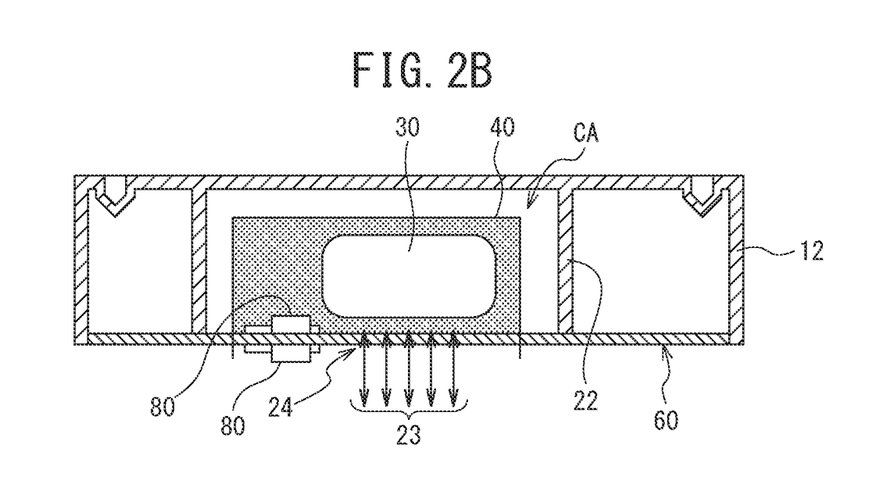

Next, a gas detector of a second embodiment will be described. FIGS. 2A and 2B illustrate schematic sectional views of a main part of a gas detector 100 of the second embodiment. In the drawings, FIG. 2A illustrates a first aspect of the second embodiment, and FIG. 2B illustrates a second aspect thereof. Additionally, portions the same as or corresponding to those in the first embodiment are denoted by the same reference signs, and a description thereof will be omitted as appropriate (the same applies to other Examples through modifications below).

As illustrated in FIG. 2A, in the gas detector 100 of the second embodiment (first aspect), a compartment cover 20 covering the gas sensor main body 30 and the area therearound is provided in a housing not illustrated in the drawing.

In the second embodiment (first aspect), sidewall portions of the compartment cover 20 correspond to the partition wall 22 of the first embodiment. Additionally, an upper surface of the compartment cover 20 is a part of the housing, where the opening portion 23 is formed, this upper surface being a mounting surface 21 for mounting the particle filter 24 on the opening portion 23. In FIG. 2A, a plurality of arrows illustrate an image of the introduction and discharge of a gas to be measured from the opening portion 23 at the top. The opening portion 23 allows for direct introduction and discharge of the gas to be measured from and to the outside to and from within the cavity space CA.

Then, the gas detector 100 of the second embodiment further includes a metal cage 40 provided in the cavity space CA in addition to the partition wall 22 of the first embodiment. The cage 40 of the second embodiment is soldered to a copper surface portion 61 of the PCB substrate 60 mounted with the gas sensor main body 30.

As a result, the cage 40 is arranged to further define a very small space including the gas sensor main body 30 and the area therearound in the cavity space CA by an area inside the partition wall 22. Additionally, in the example of the drawing, shading illustrates the very small space including the gas sensor main body 30 and the area therearound in the cavity space CA.

In addition, the gas detector 100 of the second embodiment uses a heating transistor as the heater 80. The example of the drawing uses two heaters 80, one heater 80 being directly attached to the metal cage 40, and the other heater 80 being directly attached to the copper surface portion 61 of the PCB substrate 60. Each heater 80 is controlled by an unillustrated heater controller.

A description will be given of functions and effects of the gas detector 100 of the second embodiment. Note that a description of functions and effects the same as or corresponding to those in the first embodiment will be omitted as appropriate (the same applies to other Examples through modifications below).

As described above, in the gas detector 100 of the second embodiment, the metal cage 40, which further surrounds the gas sensor main body 30 and is heated by the heaters 80 in the cavity space CA, is provided inside the partition wall 22.

Therefore, according to the gas detector 100 of the second embodiment, the cage 40 allows heat of the heaters 80 to be more effectively transferred to the gas sensor main body 30 and the area therearound. Furthermore, a thermally stable space can be more suitably obtained in an area including the cage 40 itself and being inside the cage 40 surrounded by the cage 40. This allows for an even faster response of the gas sensor main body 30 in the housing 10.

Additionally, while the second embodiment has illustrated the example in which the metal cage 40 further surrounding the gas sensor main body 30 in the cavity space CA and being heated by the heaters 80 is provided inside the partition wall 22, the present invention is not limited thereto. In order to improve the response speed of the gas sensor main body 30 in the gas detector 100, it is possible to simply provide the metal cage 40 that surround the surrounding of the gas sensor main body 30 and that is heated by the heaters 80 without providing the partition wall 22 (i.e., without defining the cavity space CA).

Even in such a configuration, the gas sensor main body 30 and the space therearound can be efficiently heated since, at least, the metal cage 40 arranged to surround the surrounding of the gas sensor main body 30 and heated by the heaters 80 is provided in the housing 10. Therefore, there can be obtained a space thermally stable in as narrow a range as possible around the gas sensor main body 30, thereby enabling improved response speed of the gas sensor main body 30 in the housing 10.

In addition, as illustrated in the first embodiment or the second embodiment (first aspect), the location of the inlet/output for the gas to be measured is not limited to an upper portion relative to the gas sensor main body 30 in the cavity space CA having a small capacity or in the metal cage 40. The inlet/outlet for the gas to be measured can be formed in any right place that allows for direct introduction and discharge of the gas to be measured from and to the outside to and from within the cavity space CA or the metal cage 40.

For example, as illustrated in the second aspect of FIG. 2B, the PCB substrate 60 on which the gas sensor main body 30 is mounted may be used as a part of the housing 10, and the opening portion 23 may be formed on the PCB substrate 60 to introduce and discharge the gas to be measured, without providing any opening portion above the gas sensor main body 30. In FIG. 2B, a plurality of arrows illustrate an image in which the gas to be measured is introduced from the opening portion 23 on the substrate side to within the cavity space CA or the metal cage 40 and then discharged from the opening portion 23.

Additionally, although not illustrated, if the partition wall 22 has a portion that is indirect contact with the outside, the opening portion 23 may be formed on the portion of the partition wall 22 in direct contact with the outside without providing any opening above the gas sensor main body 30.

Furthermore, the metal cage 40 heated by the heaters 80 is not limited to the example in which the one heater 80 such as a heating transistor is directly attached to the cage 40. In other words, as illustrated in the second aspect of FIG. 2B, the cage 40 maybe soldered to the copper surface portion 61 of the PCB substrate 60 mounted with the gas sensor main body 30.

Therefore, the metal cage 40 can be effectively heated even by the heater 80 attached to the copper surface portion 61 of the PCB substrate 60. In addition, the heater 80 may be attached on either a face side or a back side of the PCB substrate 60. FIG. 2B illustrates an example in which the heaters 80 are attached on both of the face side and the back side of the PCB substrate 60, respectively.

FIRST EXAMPLE

Figure 3A:
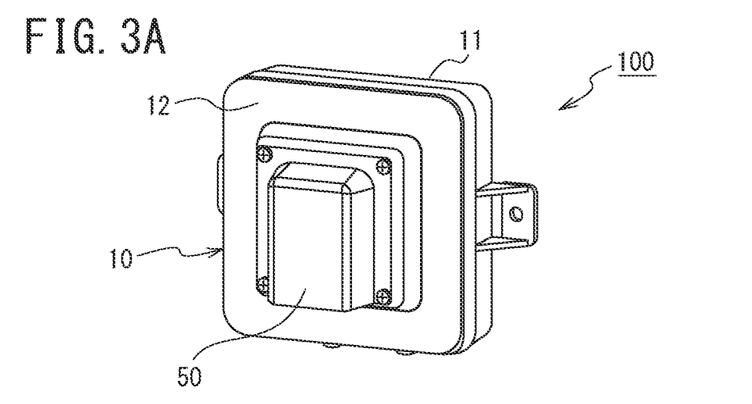
FIGS. 3A, 3B, and 3C are illustrative views illustrating a first Example of the gas detector according to the one aspect of the present invention, FIG. 3A being a perspective view, FIG. 3B being a front view, and FIG. 3C being a sectional view taken along line Z-Z of FIG. 3B.
Figure 3B:
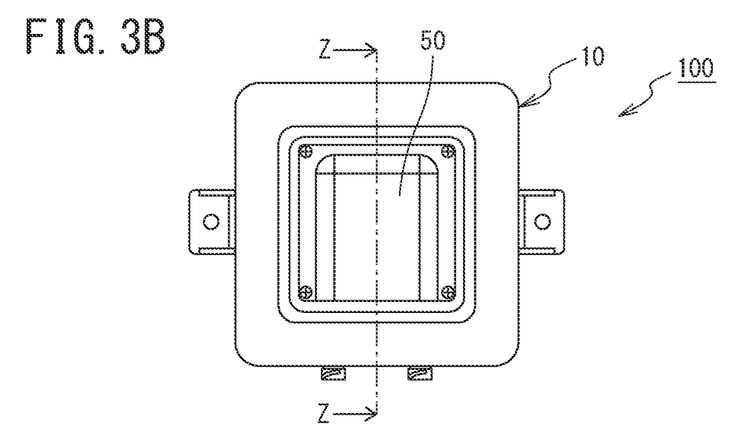
Figure 3C:
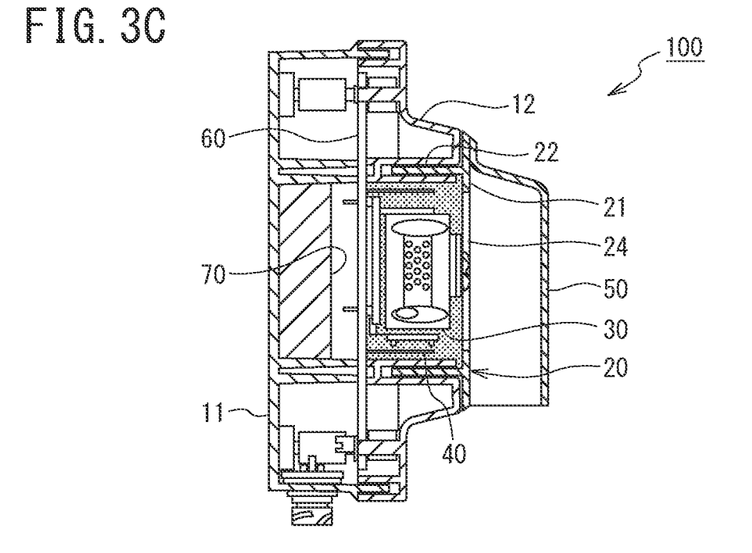

Hereinafter, the present invention will be described in more detail with reference to Examples. FIGS. 3A to 3C illustrate a first Example.

As illustrated in FIGS. 3A to 3C, a gas detector 100 of the first Example includes the housing 10 that has a substantially rectangular parallelepiped shape, the gas sensor main body 30 mounted on the PCB substrate 60 that has a rectangular plan view in the housing 10, and the partition wall 22 surrounding the surrounding of the gas sensor main body 30 in the housing 10 (see FIG. 3C).

The gas sensor main body 30 has a substantially rectangular parallelepiped appearance, and includes an optical cell, whose illustration will be omitted below. As described above, the optical cell is provided with the inlet/outlet for a gas to be measured at the top, and includes the cover portion with a cavity formed thereinside and the element portion including a reflector, a light emitter, and a light receiver provided in the cavity of the cover portion so that a predetermined optical path is formed.

The gas sensor main body 30 is configured to, when a gas to be measured is introduced into the optical cell, allow the gas to be measured to pass between the light emitter and the light receiver and the reflector and allow a concentration calculator to calculate the concentration of the gas to be measured on the basis of an output signal of the light receiver at that time.

Note that the light emitter is not particularly limited as long as it outputs light containing wavelengths absorbed by the gas to be measured. Specific examples of the light emitter include microelectromechanical systems (MEMS) light sources and light emitting diodes.

Additionally, the light receiver may be preferably a photodiode. Preferably, the photodiode has sensitivity to the band of light containing wavelengths absorbed by the gas to be measured. The shape of the photodiode is not particularly limited as long as a sufficient S/N ratio can be obtained.

The housing 10 is, for example, a plastic environmental box (an outer box with low thermal conductivity) having a rectangular parallelepiped shape with approximate dimensions of 130 mm in width, 130 mm in height, and 52 mm in depth. The housing structure of the gas detector 100 of the first Example is determined by a concept of thermal stabilization according to the present invention, as has been schematically illustrated in the first embodiment. Particularly, the section of the partition wall 22 is placed to surround, in as small an area as possible, physical dimensions of the gas sensor main body 30 required to be thermally stabilized first of all. In FIG. 3C, the area of the cavity space CA defined by the partition wall 22 is illustrated by shading.

Figure 4:
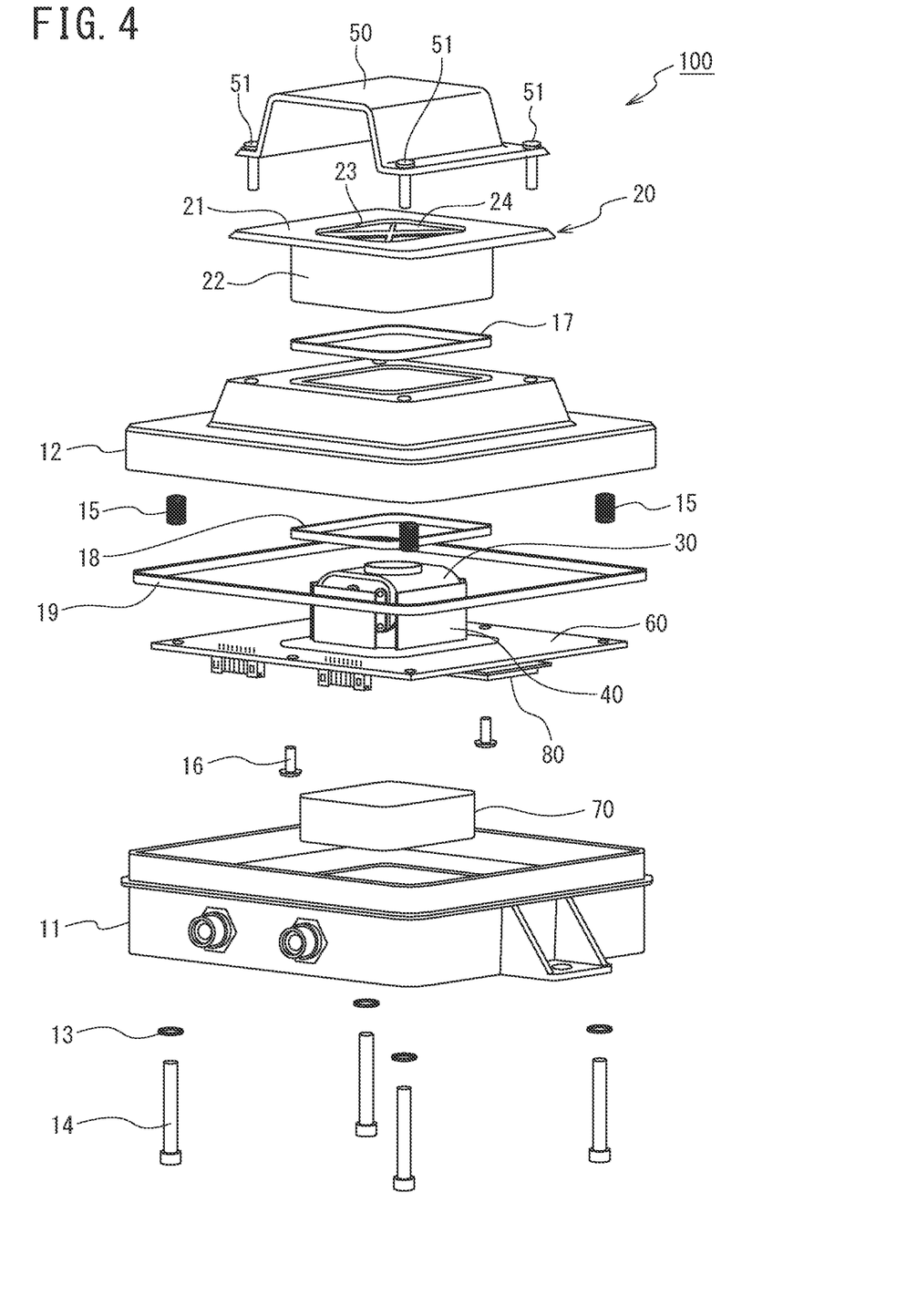
FIG. 4 is an exploded perspective view of main components included in the gas detector of FIGS. 3A to 3C.

More specifically, the housing 10 of the first Example includes the base portion 11 on the lower side, the cover portion 12 on the upper side, and the compartment cover 20, as illustrated in an exploded perspective view of FIG. 4. The PCB substrate 60 is sandwiched and fixed between the base portion 11 and the cover portion 12. A rectangular parallelepiped insulating member 70 is fitted into a center part of the base portion 11.

In the cover portion 12, an insert 15 is inserted into four corners of a back surface side thereof. The base portion 11 and the cover portion 12 are fixed by fixing bolts 14 that axially face the inserts 15 at the four corners and have washers 13 interposed from a lower surface side of the base portion 11.

At an upper center of the cover portion 12 is formed a rectangular opening, and the compartment cover 20 is mounted to cover the opening. Then, the partition wall 22 of the first Example is formed by the compartment cover 20. In other words, the compartment cover 20 of the first Example includes the mounting surface 21 at the top and the partition wall 22 that protrudes to partition a rectangular area downward from a back surface of the mounting surface 21.

Around an upper edge portion of the partition wall 22, an O ring 17 is interposed between the cover portion 12 and the compartment cover 20 of the housing 10 to maintain airtightness. Additionally, around a lower edge portion of the partition wall 22, an O ring 18 is interposed between the base portion 11 and the compartment cover 20 of the housing 10 to maintain airtightness.

In the compartment cover 20 of the first Example, a center part of the mounting surface 21 at the top is provided with the opening portion 23 opening in a rectangular shape as an inlet/outlet for a gas to be measured, and the particle filter 24 for gas exchange is mounted to cover the opening portion 23.

In addition, at the opening portion 23 at the top of the compartment cover 20, the inlet cover 50 is provided detachably by cover fixing screws 51. The inlet cover 50 prevents dust particles and raindrops from infiltrating into the opening portion 23.

The PCB substrate 60 is arranged to be located in abutment with a rectangular frame-shaped bottom surface of the partition wall 22. The gas sensor main body 30 is mounted by soldering pin headers 31 of the gas sensor main body 30 to a substantially center part of an upper surface of the PCB substrate 60.

Additionally, at the top of the partition wall 22, the mounting surface 21 is formed by a plastic wall covering to close an upper opening of the housing 10. An O ring 19 is interposed between an upper opening of the base portion 11 of the housing 10 and the PCB substrate 60 to maintain airtightness.

As described above, in the first Example, the gas sensor main body 30 is provided in the small cavity space CA defined by the rectangular frame-shaped partition wall 22 formed by the compartment cover 20. Then, in the other area excluding the cavity space CA in the housing 10, auxiliary electronic devices, electronic components such as interfaces, a communication unit, and a heater controller, and members such as connectors, which will not be illustrated below, are arranged.

Furthermore, in the first Example, the heater 80 is arranged with an opposite side of the PCB substrate 60 to the gas sensor main body 30. In the first Example, the gas sensor main body 30 and the inside of the cavity space CA can be heated from the back surface side of the PCB substrate 60 by the PCB substrate 60 including the heater 80 formed by a resistance heater or a heating transistor. The heater 80 uses a regulator having a simple configuration to maintain the temperature of the gas sensor main body 30 constant, as in the first embodiment.

Figure 5A:
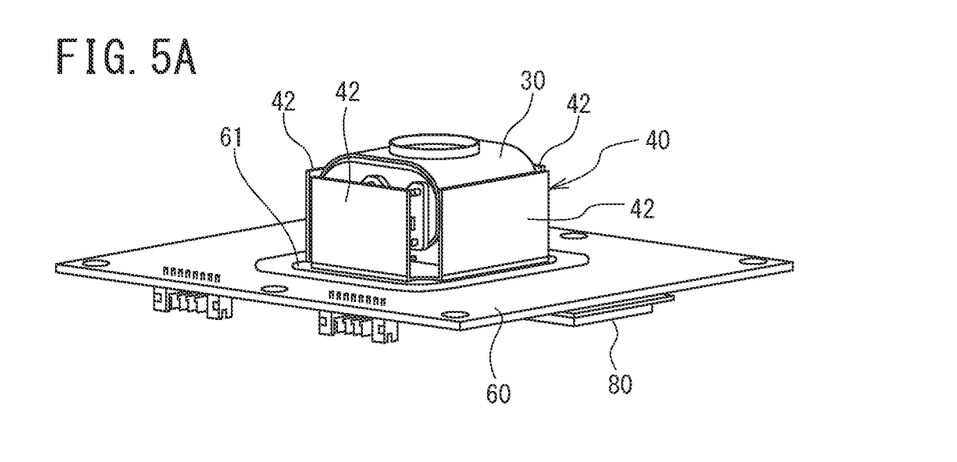
FIGS. 5A and 5B are illustrative views of a sensor main body and a substrate portion of FIGS. 3A to 3C, FIG. 5A being a perspective view, and FIG. 5B being an exploded perspective view.
Figure 5B:
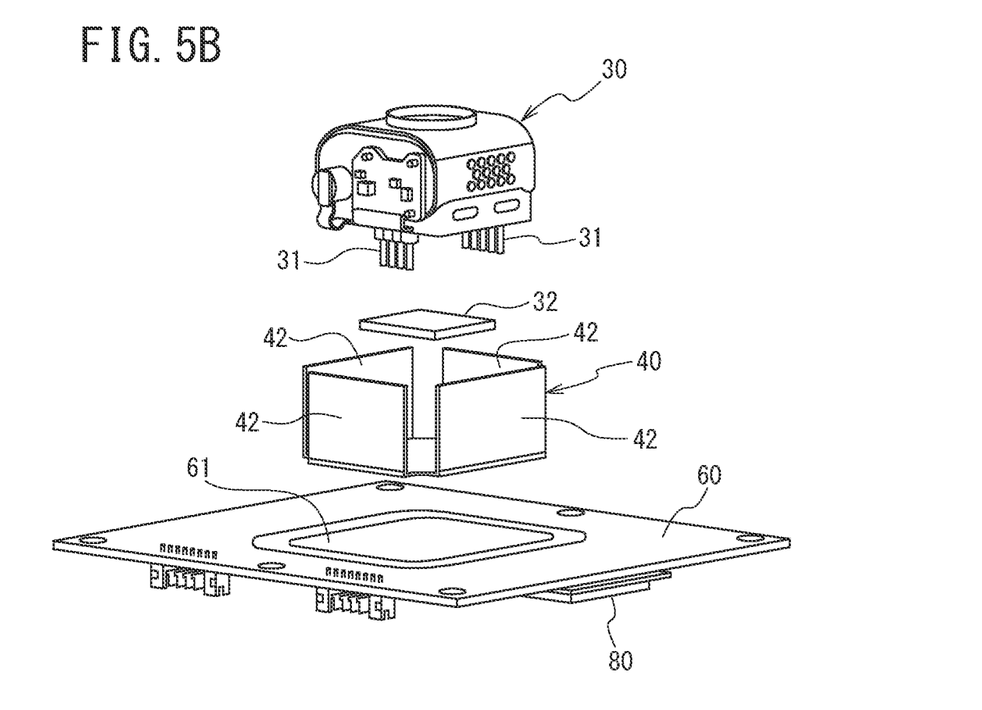

Still furthermore, as illustrated in FIGS. 5A and 5B, the first Example includes the metal cage 40 that further surrounds the surrounding of the gas sensor main body 30 by four side wall surfaces 42 in the cavity space CA.

The cage 40 of the first Example is formed of a metal plate member, and includes a rectangular bottom surface portion abutted with the upper surface of the PCB substrate 60. The four side wall surfaces 42 are folded back upward from positions of respective four sides of the rectangular bottom surface portion to form the cage 40. Therefore, the cage 40 of the first Example is configured not to cover above the gas sensor main body 30.

The bottom surface portion has a wide surface to allow for efficient heat transfer, and attached in close contact with the upper surface of the PCB substrate 60. Additionally, between an upper surface of the bottom surface portion of the cage 40 and a back surface of the gas sensor main body 30, a rectangular retaining plate 32 with high heat transfer characteristics is interposed in close contact with both of the surfaces.

The retaining plate 32 is adapted to ensure that a mounting posture of the gas sensor main body 30 is retained and that the cage 40 and the gas sensor main body 30 are placed in close contact with each other to further improve heat transfer.

The PCB substrate 60 including the heater 80 formed by a resistance heater or a heating transistor allows heat that heats the inside of the cavity space CA to be directly and transferrably connected to the metal cage 40 by the heater 80 and maintain the area around the gas sensor main body 30 at a desired temperature.

The first Example includes a 3-W resistance heater provided as the heater 80 in a right place on the back surface of the PCB substrate 60, and an unillustrated PID regulator that controls the heater 80. The PID regulator is composed of a very simple regulator, and capable of controlling a temperature parameter of the gas sensor main body 30 to within a predetermined range.

Next, a description will be given of functions and effects of the gas detector 100 of the first Example.

As described above, in the gas detector 100 of the first Example, the gas sensor main body 30 is placed in the cavity space CA surrounded by the partition wall 22 of the compartment cover 20, while being separated from the other area.

Here, usually, the gas sensor main body 30 using infrared light is very sensitive to humidity and airflow fluctuations. Accordingly, desired performance of this type of gas sensor main body 30 is guaranteed by required calibration in outdoor environment.

On the other hand, according to the configuration of the first Example, providing the cavity space CA defining the narrow range by the partition wall 22 surrounding the surrounding of the gas sensor main body 30 in the housing 10 brings about excellent effects even in a harsh outdoor cold environment.

Specifically, in the gas detector 100 of the first Example, even when the installation environment of the gas detector 100 is, for example, at an extremely low temperature of approximately −40° C., the gas sensor main body 30 in the housing 10 is maintained at, for example, approximately +20° C., achieving thermal stabilization of the gas sensor main body 30. Therefore, responsiveness of the gas sensor main body 30 is improved, and operation thereof is stabilized, whereby, for example, in the case of the first Example, stable operation can be achieved with a power consumption of approximately 70% of maximum power.

Furthermore, as illustrated in FIGS. 5A and 5B, the first Example further includes the metal cage 40 that surrounds the surrounding of the gas sensor main body 30 by the four side wall surfaces. Accordingly, the metal cage 40 allows heat from the heater 80 to be more effectively transferred to the gas sensor main body 30, and also allows a space thermally stable in as narrow a range as possible to be more suitably obtained in the area inside the cage 40 and the four side wall surfaces 42 in the cavity space CA.

Particularly, in the first Example, heat from the heater 80 can be more effectively transferred to the metal cage 40 via the copper surface portion 61 of the PCB substrate 60, as illustrated in FIGS. 5A and 5B. Therefore, even though it is a heat transfer structure from one side of the PCB substrate 60, the gas sensor main body 30 and the inside of the cavity space CA can be efficiently heated. This allows for effective transfer of heat from the heater 80 to a desired range in order to ensure that the gas sensor main body 30 is stably operated at uniform temperature. Operation of the gas sensor main body 30 in the first Example has achieved a fast response time of only 15 seconds.

Figure 6A:
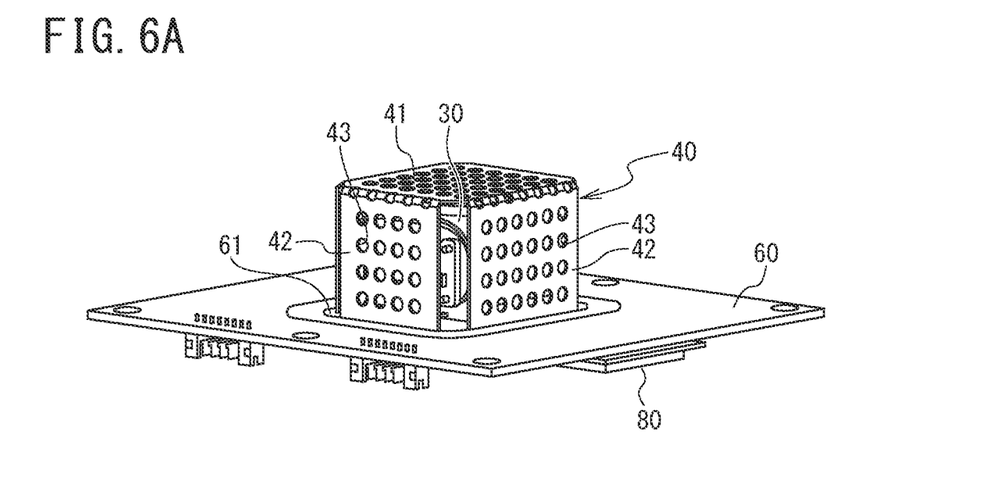
FIGS. 6A and 6B are illustrative views of another example (a second Example) of the sensor main body and the substrate portion of FIGS. 3A to 3C, FIG. 6A being a perspective view, and FIG. 6B being an exploded perspective view.
Figure 6B:
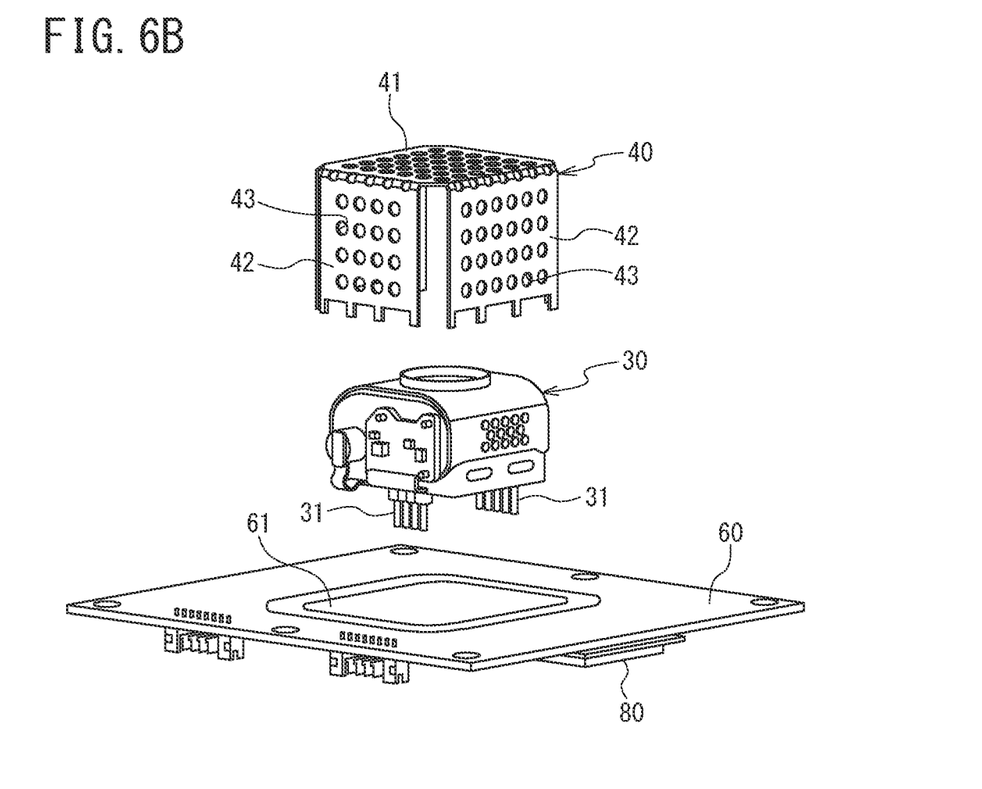

Next, another example (second Example) of the metal cage 40 will be described. FIGS. 6A and 6B are illustrative views of the gas sensor main body 30 and a substrate section according the second Example. FIG. 6A is a perspective view, and FIG. 6B is an exploded perspective view.

As illustrated in the drawings, the second embodiment is configured such that the surrounding of the gas sensor main body 30 surrounded by the partition wall 22 of the compartment cover 20 is surrounded by the metal cage 40 so as to define an even smaller area around the gas sensor main body 30 in the cavity space CA, as in the first Example.

Particularly, in the second Example, a roof portion 41 and sidewall surface portions 42 of the metal cage 40 form one roof portion 41 and four sidewall surface portions 42 with favorable thermal conductivity around the gas sensor main body 30 to surround it.

In other words, while the cage 40 of the first Example 40 has not covered above the gas sensor main body 30, the cage 40 of the second Example is configured to cover above the gas sensor main body 30. Then, multiple air holes 43 are formed through the roof portion 41 and the sidewall surface portions 42 of the metal cage 40.

As a result, in the second Example, air taken into the cavity space CA area in the partition wall 22 of the housing 10 from outside the housing 10 is exposed to a surface temperature of the cage 40 with favorable thermal conductivity heated by the heater 80 when the air passes through the multiple air holes 43 formed on the roof portion 41 and the sidewall surface portions 42 of the metal cage 40. This achieves further thermal stabilization of the gas sensor main body 30 and the air in the cage 40.

Additionally, in the second Example, the metal cage 40 integrally combined with the copper surface portion 61 of the PCB substrate 60 also serves as a Faraday cage.

Specifically, all directions of the gas sensor main body 30 are surrounded by the roof portion 41 and the sidewall surface portions 42 of the cage 40, which can therefore protect the gas sensor main body 30 from electromagnetic interference/radio frequency interference (EMI/RFI) from surrounding environment, and also can protect the surrounding environment from electric radiation of the gas sensor main body 30 in all directions.

Note that a Faraday cage means a space surrounded by conductors or a conductor cage or container itself used to create such a space. Since no electric force line can enter the inside surrounded by conductors, an external electric field is blocked, and all internal potentials become equal.

Thus, as described based on the embodiments and the Examples, the gas detector according to the one aspect of the present invention can improve the response speed of the gas sensor in the housing. It should be noted that, obviously, the gas detector according to the present invention is not limited to the above embodiments or Examples, and can be variously modified without departing from the spirit of the present invention.

For example, the above embodiments or Examples have illustrated the example in which the particle filter 24 for gas exchange is mounted to cover the opening portion 23 of the compartment cover 20, and the inlet cover 50 is mounted to cover the opening portion 23 from a direction opposite thereto.

However, the configuration of the inlet/outlet for a gas to be measured in the gas detector according to the one aspect of the present invention is not limited thereto, and various modifications can be made within the spirit of the present invention.

Figure 7A:
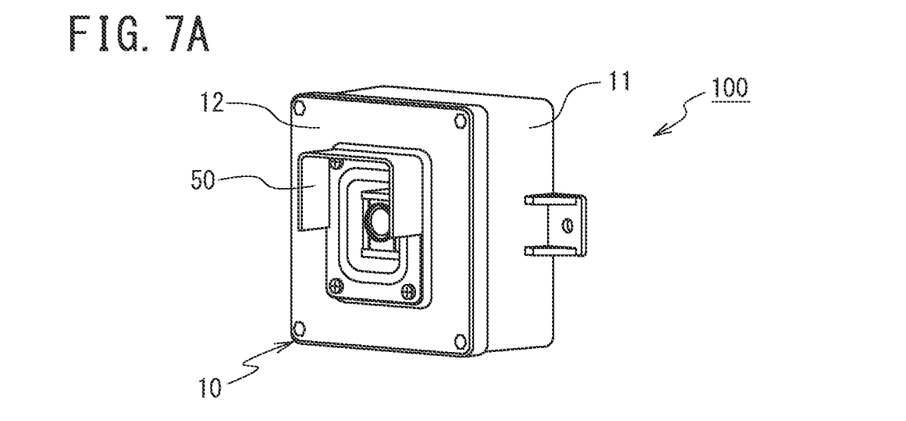
FIGS. 7A, 7B, and 7C are illustrative views illustrating a modification (a first modification) of a housing structure of the gas detector according to the one aspect of the present invention, FIG. 7A being a perspective view, FIG. 7B being a front view, and FIG. 7C being a sectional view taken along line Z-Z of FIG. 7B.
Figure 7B:
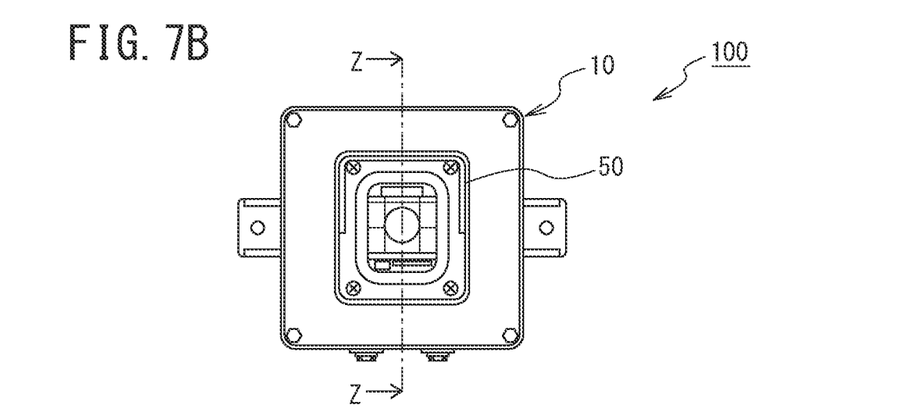
Figure 7C:
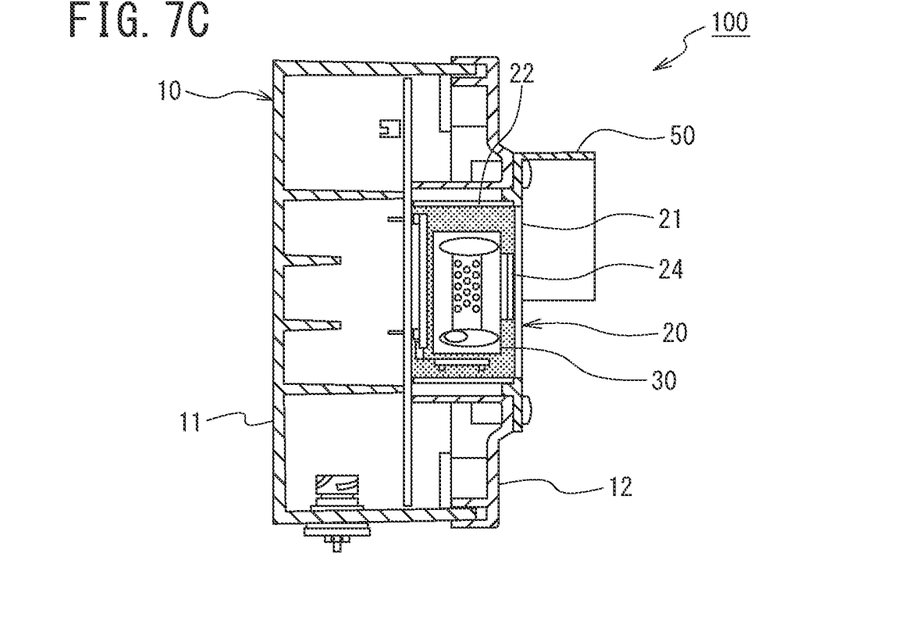

For example, as illustrated in a first modification of FIGS. 7A to 7C, the inlet cover 50 may be mounted to cover the opening portion 23 of the compartment cover 20 from the sides. Having such a configuration would be suitable for preventing dust particles and raindrops from infiltrating into the opening portion 23 when the mounting posture of the housing 10 is vertical.

Figure 8A:
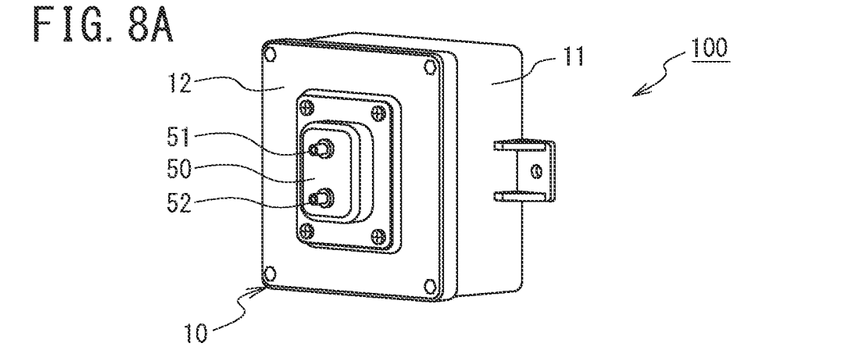
FIGS. 8A, 8B, and 8C are illustrative views illustrating a modification (a second modification) of the housing structure of the gas detector according to the one aspect of the present invention, FIG. 8A being a perspective view, FIG. 8B being a front view, and FIG. 8C being a sectional view taken along line Z-Z of FIG. 8B.
Figure 8B:
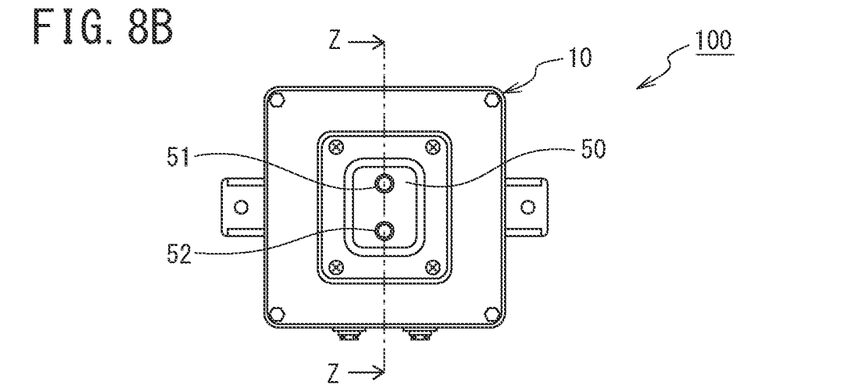
Figure 8C:
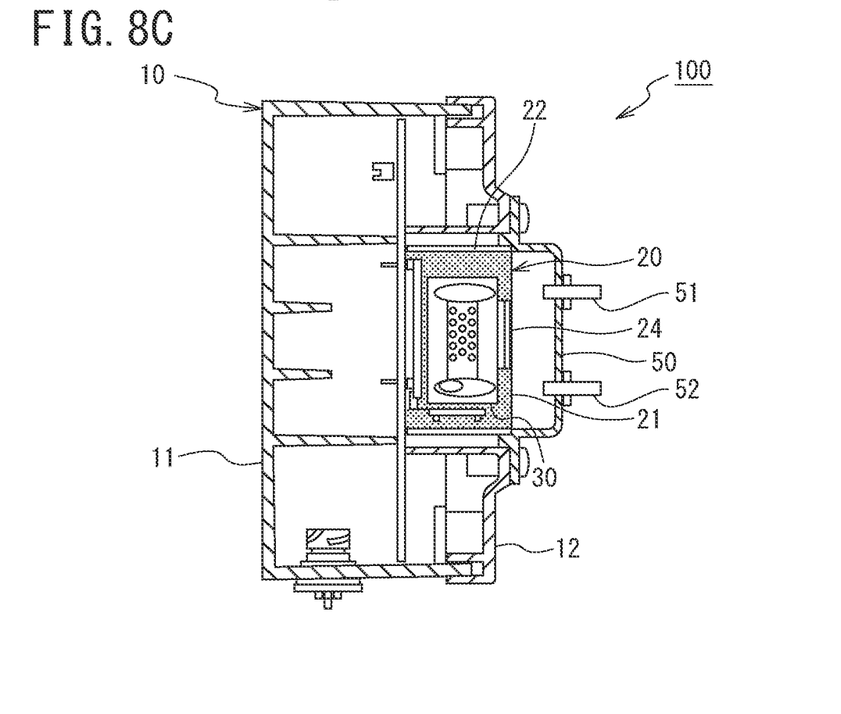

In addition, for example, as illustrated in a second modification of FIGS. 8A to 8C, the inlet cover 50 that covers the opening portion 23 of the compartment cover 20 entirely from the direction opposite thereto may be provided, and an introduction pipe 51 for a gas to be measured and a discharge pipe 52 for the gas to be measured may be provided in two positions of the inlet cover 50. Having such a configuration would be suitable for preventing dust particles and raindrops from infiltrating into the opening portion 23 regardless of the mounting posture of the housing 10.

REFERENCE SIGNS LIST

10: Housing
11: Base portion
12: Cover portion
13: Washer
14: Fixing bolt
15: Insert
16: Fixing pin
17: O ring
18: O ring
19: O ring
20: Compartment cover
21: Mounting surface
22: Partition wall
23: Opening portion
24: Particle filter
30: Gas sensor main body
31: Pin header
40: Cage
41: Roof
42: Side wall surface
43: Air hole
50: Inlet cover
51: Cover fixing screw
60: PCB substrate
61: Copper surface portion
70: Insulating member
80: Heater
81: PID regulator
90: Other area
100: Gas detector
CA: Cavity space

The invention claimed is:

1. A gas detector, comprising:
a housing;
a gas sensor main body installed in the housing; and
a partition wall provided in the housing and surrounding the gas sensor main body to separate an area inside the partition wall and containing the gas sensor main body from an other area within the housing,
wherein the housing or the partition wall includes an opening portion directly connected from an outside to the area inside the partition wall, and
wherein the opening portion is formed on a portion of the partition wall other than a portion separating the area inside the partition wall and containing the gas sensor main body from the other area within the housing.

2. The gas detector according to claim 1, wherein a volume of the area inside the partition wall is equal to or less than half a volume of the other area.

3. The gas detector according to claim 1, further comprising an inlet cover configured to cover the opening portion.

4. The gas detector according to claim 1, wherein an electronic component in arranged in the other area of the housing; and wherein only the first area inside the partition wall is connected to the outside by the opening portion.

5. The gas detector according to claim 1, further comprising a metal cage surrounding the gas sensor main body in the area inside the partition wall and heated by a heater.

6. The gas detector according to claim 5, wherein the cage includes a plurality of air holes.

7. The gas detector according to claim 5, wherein the cage is soldered to a copper surface portion of a printed circuit board mounted with the gas sensor main body, the cage being combined with the copper surface portion to serve as a Faraday cage to protect the gas sensor main body from electromagnetic interference/radio frequency interference (EMI/RFI) from surrounding environment.

8. A gas detector, comprising:
a housing;
a gas sensor main body installed in the housing; and
a partition wall provided in the housing and surrounding the gas sensor main body, wherein a first portion of the partition wall separates a first area containing the gas sensor main body from a second area within the housing,
wherein a second portion of the partition wall includes an opening portion directly connected from an outside to the first area inside the partition wall, and
wherein the second portion of the partition wall is on a surface of the partition wall other than a surface of the first portion of the partition wall.

* * * * *